US00PP30548P3

(12) United States Plant Patent
Olesen

(10) Patent No.: US PP30,548 P3
(45) Date of Patent: Jun. 4, 2019

(54) MINIATURE ROSE PLANT NAMED 'POULPAR092'

(50) Latin Name: ***Rosa* hybrid**
Varietal Denomination: Poulpar092

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 21 days.

(21) Appl. No.: 15/731,973

(22) Filed: Sep. 5, 2017

(65) Prior Publication Data

US 2019/0075694 P1 Mar. 7, 2019

(51) Int. Cl.
*A01H 5/02* (2018.01)

(52) U.S. Cl.
USPC ..... Plt./118
CPC ..... *A01H 5/02* (2013.01)

(58) Field of Classification Search
USPC ..... Plt./118
See application file for complete search history.

(56) References Cited

PUBLICATIONS

UPOV hit on miniature rose plant named 'Poulpar092', QZ PBR 49432, filed Sep. 19, 2016.*

* cited by examiner

*Primary Examiner* — Anne Marie Grunberg

(57) ABSTRACT

A new garden rose plant of the Miniature class which has abundant, yellow flowers and attractive foliage. This new and distinct variety has shown to be uniform and stable in the resulting generations from asexual propagation.

3 Drawing Sheets

Botanical designation: *Rosa* hybrid.
Variety denomination: 'Poulpar092'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpar092', originated as a single seedling from the stated cross.

The new variety may be distinguished from its male pollen parent and female seed parent primarily by the following characteristics. The male pollen parent plant has Orange Group 27A flowers while the new variety has Yellow-Orange Group 16A flowers. The female seed parent plant has a climbing and spreading habit, while the new variety grows upright.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance.

This combination of qualities is not present in previously available commercial cultivars of this type, known to the inventor, and distinguish 'Poulpar092' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpar092' was selected in the spring of 2008 by the inventor as a single plant from the progeny of the aforementioned hybridization.

Asexual reproduction of 'Poulpar092' by rooted cuttings was first done by Mogens N. Olesen in the nursery in Fredensborg, Denmark in July, 2008. This initial and other subsequent asexual propagations conducted in controlled environments have demonstrated that the characteristics of 'Poulpar092' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar092'.

Specifically illustrated in FIG. 1 of the drawings are open flower, petals detached, sepals detached, flower bud and reproductive flower parts.

Figure 1:
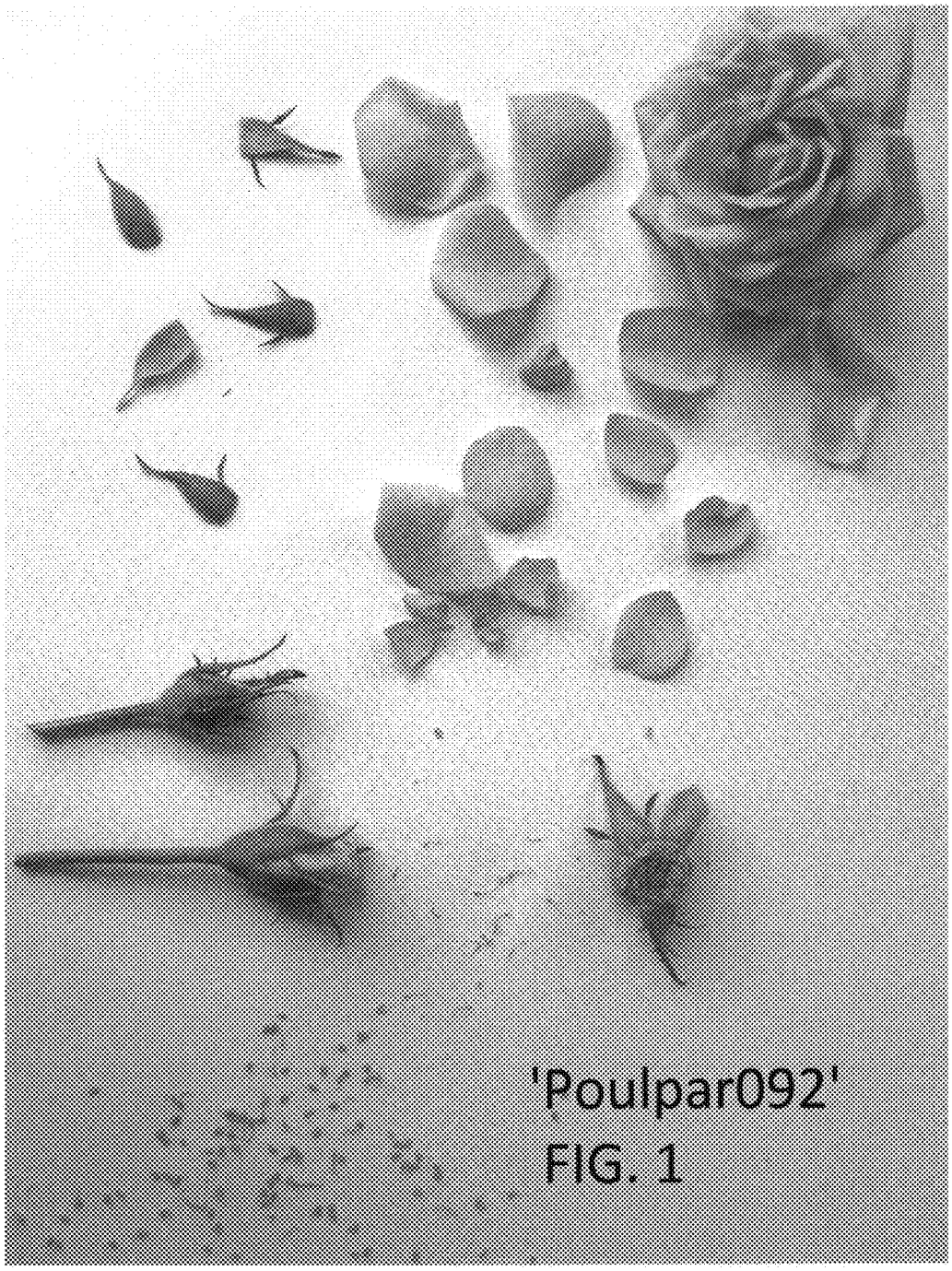
Figure 2:
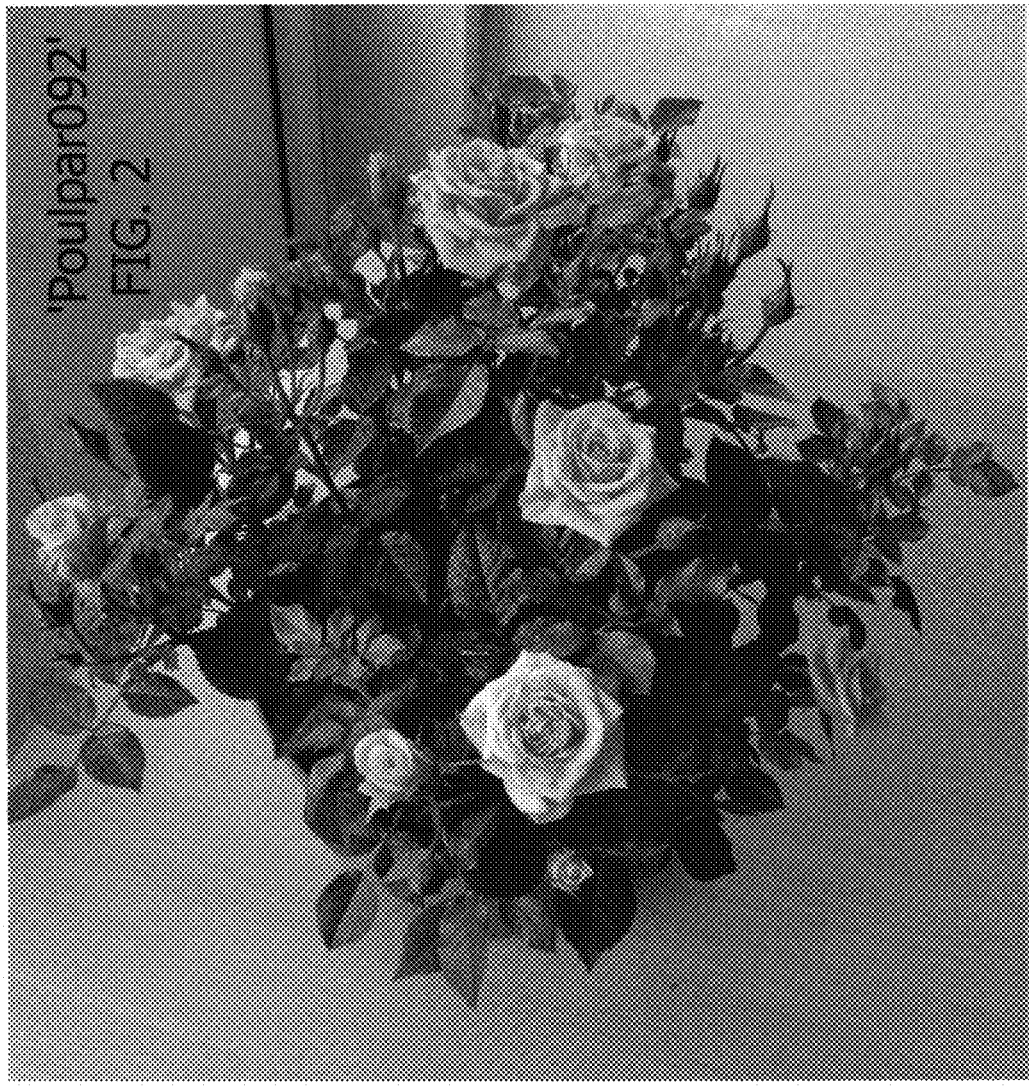

Specifically illustrated in FIG. 2 of the drawings is a flowering plant.

Figure 3:
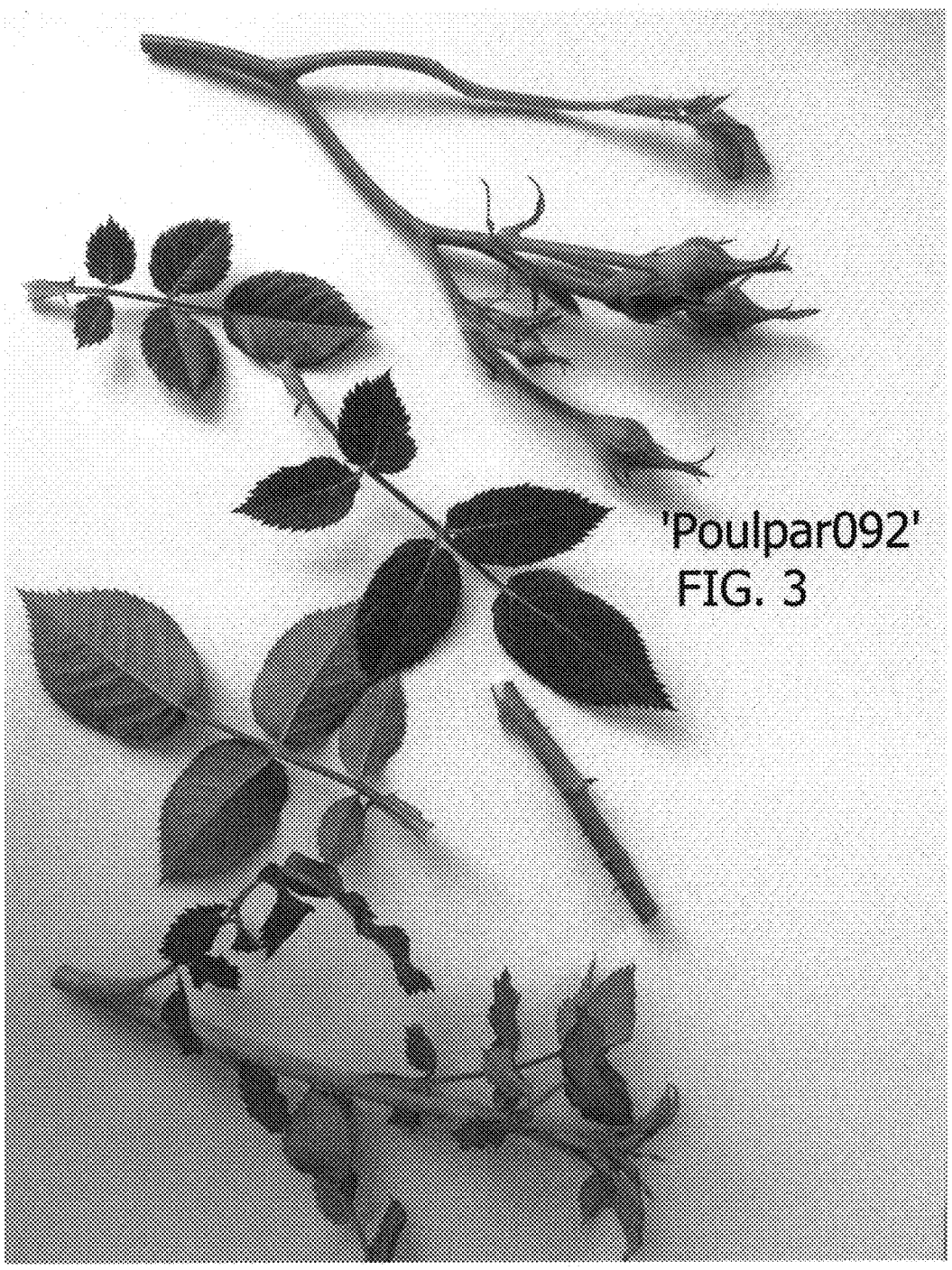

FIG. 3 shows stems and leaves. Plants shown are 2 years of age.

DETAILED DESCRIPTION OF THE VARIETY

The following is a description of 'Poulpar092', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar065', U.S. Plant Pat. No. 23,822, are compared to 'Poulpar092' in Chart 1.

CHART 1

| | 'Poulpar092' | 'Poulpar065' |
|---|---|---|
| Petal Count | 45 | 80 to 90 |
| Flower Diameter | 50-60 mm | 50 to 55 mm |
| General Tonality of Flower Color | Yellow-Orange Group 16A | Yellow Group 10B with intonations of Yellow Group 13C |

FLOWER AND FLOWER BUD

Blooming habit: Continuous.

Flower bud:

*Size.*—Upon opening, 25 mm in length from base of receptacle to end of bud. Bud diameter is 10 mm.

*Bud form.*—Ovoid.

*Bud color.*—As sepals divide petals are Yellow-Orange Group 23B.

*Sepal inner surface.*—Color: Green Group 138C. Surface: Lightly pubescent.

*Sepal outer surface.*—Color: Green Group 143B. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—20 mm long, 8 mm wide.

*Receptacle.*—Texture: Smooth. Size: 5 mm in height, 8 mm wide. Color: Yellow-Green Group 144A. Shape: Campanulate.

*Pedicel.*—Surface: Smooth. Length: 20 to 50 mm. Diameter: 2 mm on average. Color: Yellow-Green Group 144A. Strength: Moderate.

*Peduncle.*—Length: 20 to 120 mm. Diameter: About 3 mm. Color: Yellow-Green Group 144A with weak intonations of Greyed-Red Group 178B. Texture: Smooth.

Flower bud development: Flower buds are borne in clusters of 4 to 10 flower buds per stem.

Flower bloom:

*Fragrance.*—Light floral scent.

*Duration.*—The blooms have a duration on the plant of approximately 15 days. Petals fall cleanly away from plant after flowers have fully matured.

*Size.*—Flower diameter is 50 to 60 mm when open. Flower depth is 25 mm.

*Flower shape.*—High centered, semi double, with a high pointed center which is tightly closed.

*Shape of flower, side view.*—The upper portion is flattened convex. The lower portion is concave.

Petalage: Under normal conditions, flowers have about 45 petals.

General tonality of flower: Open flowers are Yellow-Orange Group 16A.

Petal color:

*Upon opening, outer petals.*—Upper surface: Yellow Group 13B. Lower surface: Orange Group 24B.

*Upon opening, inner petals.*—Upper surface: Yellow-Orange Group 15B. Lower surface: Orange Group 24B.

*Basal petal spots, upon opening.*—No distinctive coloration at the petal base observed.

*After opening, outer petals.*—Upper surface: Yellow Group 12A. Lower surface: Yellow-Orange Group 22B.

*After opening, inner petals.*—Upper surface: Yellow Group 13B. Lower surface: Orange Group 24C.

*Basal petal spots, after opening.*—No distinctive coloration at the petal base observed.

Petals:

*Petal reflex.*—Bilateral on outer petals.

*Margin.*—Entire and uniform. Moderate undulations.

*Shape.*—Broad and elliptic. Apex shape: Rounded. Base shape: Acute.

*Size.*—26 mm (l)×18 mm (w).

*Texture.*—Slightly textured.

*Thickness.*—Average.

Petaloids:

*Size.*—15 mm (l) by 10 mm (w).

*Quantity.*—About 10.

*Shape.*—Elliptical with an acute base and rounded apex.

*Color.*—Upper surface is Yellow Group 13B, and lower surface is Yellow-Orange Group 24C.

Reproductive flower parts:

*Pollen.*—None observed.

*Anthers.*—Size: 2 mm in length. Color: Yellow-Orange Group 14A. Quantity: About 100.

*Filaments.*—Color: Yellow-Orange Group 14A. Length: 2 to 3 mm.

*Pistils.*—Length: 3 mm. Quantity: 70 on average.

*Stigmas.*—Color: Red Group 47A.

*Styles.*—Color: Yellow Group 2C.

*Location of stigmas.*—Level in location relative to the length of the filaments and the height of the anthers.

*Hips.*—None Observed.

PLANT

Plant growth: Upright, bushy. Plants are 20 cm in height, and 30 cm wide.

Stems:

*Color of juvenile growth.*—Yellow-Green Group 144C.

*Color of mature growth.*—Yellow-Green Group 146A.

*Length.*—Canes are about 18 cm from the base of the plant to the flowering portion.

*Diameter.*—About 5 mm.

*Internodes.*—On mature canes about 15 to 30 mm between nodes.

*Surface texture.*—Young wood: Smooth. Older wood: Smooth.

Long prickles:

*Incidence.*—Some stems exhibit about 5 prickles per 10 cm of stem.

*Size.*—Average length of prickles on mature stems is 3 mm.

*Shape.*—Upper portion is linear. Lower portion is linear.

*Color.*—Juvenile prickles: Greyed-Purple Group 183C. Mature prickles: Greyed-Purple Group 183C.

Plant foliage:

*Compound leaf.*—70 to 100 mm (l)×40 to 70 mm (w).

*Quantity*.—3 leaves per 10 cm of stem on average.

*Color of juvenile foliage*.—Upper side: Yellow-Green Group 146A. Lower side: Yellow-Green Group 148B. Anthocyanin: Margins, Greyed-Purple Group 183C.

*Color of mature foliage*.—Upper side: Yellow-Green Group 147A. Lower side: Yellow-Green Group 147B.

Plant leaves and leaflets:

*Stipules*.—Size: 12 mm long, 3 mm wide. Quantity: 2 per compound leaf. Shape: Linear, slightly broad based with outward extending apices. Margins: Finely serrated with many stipitate glands. Color: Yellow-Green Group 147B with intonations of Greyed-Purple Group 184B.

*Petiole*.—Length: 2 to 15 mm. Diameter: About 2 mm. Upper surface color: Yellow-Green Group 146B with intonations of Greyed-Purple Group 184B. Lower surface color:

*Rachis*.—Length: 10 to 20 mm. Upper surface color: Yellow-Green Group 146B. Lower surface color: Yellow-Green Group 146B.

*Leaflet*.—Quantity: Normally 5 leaflets. Margins: Serrated. Size: Terminal leaflets are about 30 to 40 mm long, 18 to 25 mm wide. Shape: Generally ovate. Base: Rounded. Apex: Acuminate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Miniature rose class named 'Poulpar092', substantially as illustrated and described herein, due to its abundant yellow flowers, disease resistance, and extended period of bloom.

* * * * *

'Poulpar092'

'Poulpar092'

'Poulpar092'